(12) United States Patent
Shortis

(10) Patent No.: US 10,328,088 B2
(45) Date of Patent: Jun. 25, 2019

(54) USE OF AMINOSALICYLATES IN DIARRHOEA-PREDOMINENT IRRITABLE BOWEL SYNDROME

(71) Applicant: Salix Pharmaceuticals, Inc., Bridgewater, NJ (US)

(72) Inventor: Nicolas Peter Shortis, Pymble (AU)

(73) Assignee: Salix Pharmaceuticals, Inc., Bridgewater, NJ (US)

(*) Notice: Subject to any disclaimer, the term of this patent is extended or adjusted under 35 U.S.C. 154(b) by 0 days.

(21) Appl. No.: 15/907,566

(22) Filed: Feb. 28, 2018

(65) Prior Publication Data

US 2018/0250315 A1    Sep. 6, 2018

Related U.S. Application Data

(63) Continuation of application No. 14/585,911, filed on Dec. 30, 2014, now Pat. No. 9,937,190, which is a continuation of application No. 13/742,837, filed on Jan. 16, 2013, now abandoned, which is a continuation of application No. 10/588,558, filed as application No. PCT/AU2005/000142 on Feb. 4, 2005, now abandoned.

(30) Foreign Application Priority Data

Feb. 6, 2004   (AU) ............................... 2004900563

(51) Int. Cl.
| | | |
|---|---|---|
| *A61K 31/437* | (2006.01) | |
| *A61K 31/655* | (2006.01) | |
| *A61K 31/166* | (2006.01) | |
| *A61K 31/606* | (2006.01) | |
| *A61K 31/635* | (2006.01) | |
| *A61K 45/06* | (2006.01) | |

(52) U.S. Cl.
CPC .......... *A61K 31/655* (2013.01); *A61K 31/166* (2013.01); *A61K 31/437* (2013.01); *A61K 31/606* (2013.01); *A61K 31/635* (2013.01); *A61K 45/06* (2013.01)

(58) Field of Classification Search
CPC ........................... A61K 31/437; A61K 31/655
See application file for complete search history.

(56) References Cited

U.S. PATENT DOCUMENTS

| | | | |
|---|---|---|---|
| 3,915,951 A | 10/1975 | Agback et al. | |
| 4,298,595 A | 11/1981 | Parkinson et al. | |
| 4,412,922 A | 11/1983 | Mir | |
| 4,412,992 A | 11/1983 | Chan | |
| 4,496,553 A | 1/1985 | Halskov | |
| 4,562,024 A | 12/1985 | Rogerson | |
| 4,725,676 A | 2/1988 | Agback et al. | |
| 4,781,925 A | 11/1988 | Michelucci et al. | |
| 4,880,794 A | 11/1989 | Halskov | |
| 4,960,765 A | 10/1990 | Halskov | |
| 5,013,727 A | 5/1991 | Halskov | |
| 5,064,637 A | 11/1991 | Sullivan | |
| 5,095,073 A | 3/1992 | Peiffer et al. | |
| 5,106,960 A | 4/1992 | Hurter et al. | |
| 5,196,205 A | 3/1993 | Borody | |
| 5,374,430 A | 12/1994 | Newton et al. | |
| 5,376,382 A | 12/1994 | Goede et al. | |
| 5,476,669 A | 12/1995 | Borody | |
| 5,498,608 A | 3/1996 | Ogawa et al. | |
| 5,519,014 A | 5/1996 | Borody | |
| 5,541,170 A | 7/1996 | Rhodes et al. | |
| 5,905,073 A | 5/1999 | Johnson et al. | |
| 5,927,500 A | 7/1999 | Godfrey et al. | |
| 6,144,381 A | 11/2000 | Lection et al. | |
| 6,197,341 B1 | 3/2001 | Friess et al. | |
| 6,231,888 B1 | 5/2001 | Lemer et al. | |
| 6,277,412 B1 | 8/2001 | Otterbeck | |
| 6,277,836 B1 | 8/2001 | Borody | |
| 6,326,364 B1 | 12/2001 | Lin et al. | |
| 6,407,128 B1 | 6/2002 | Scaife et al. | |
| 6,426,338 B1 | 7/2002 | Borody | |

(Continued)

FOREIGN PATENT DOCUMENTS

| | | |
|---|---|---|
| EP | 0974344 A2 | 1/2000 |
| EP | 2096912 A2 | 9/2009 |

(Continued)

OTHER PUBLICATIONS

Alexander, American Disease Week and American Diabetes Association. Pharmacy and Therapeutics. 2008;33(9):546-549.
Allgayer et al., Colonic N-Acetylation of 5-Aminosalicyclic Acid in Inflammatory Bowel Disease. Gastroenterology. 1989;97:38-41.
Asacol Summary Basis for Approval, Review of Two Bioavailability Study. Norwich Eaton Pharmaceuticals Inc., 12 pages. Jul. 18, 1988.
Baughan et al., A randomized trial to assess the efficacy of 5-aminosalicylic acid for the prevention of radiation enteritis. Clin Oncol (R Coll Radiol). 1993;5(1):19-24.
Bindhumadhavan et al., Roll compaction of a pharmaceutical excipient: Experimental validation of rolling theory for granular solids. Chemical Engineering Science. 2005;60:3891-3897.
Bottini et al., Inflammatory bowel disease: Are there gender differences in the genetics of signal transduction? A preliminary study of cytosolic low molecular weight protein tyrosine phosphatase. Dis Markers. 2000;16(3-4):163-6.

(Continued)

*Primary Examiner* — James D. Anderson
(74) *Attorney, Agent, or Firm* — McCarter & English, LLP; Jonathan M. Sparks; Michael J. DeGrazia

(57) ABSTRACT

A method for the treatment or prophylaxis of non-inflammatory bowel diseases, diarrhoea-predominant irritable bowel syndrome or other non-specific bowel disorder is disclosed comprising administering to a patient in need of such treatment or prophylaxis an effective amount of balsalazide, or a 4-ASA or 5-ASA compound modified to include a 4-ABA side chain, or a salt or a derivative thereof, or a composition comprising balsalazide the modified compound, or a salt or a derivative thereof together with a suitable carrier. Use of balsalazide, a 4-ASA or 5-ASA compound modified to include a 4-ABA side chain, or a salt or derivative thereof, for the manufacture of a medicament for the treatment or prophylaxis of non-inflammatory bowel diseases, diarrhoea-pre-dominant Irritable Bowel Syndrome or other non-specific bowel disorder is also disclosed.

12 Claims, No Drawings

(56) References Cited

U.S. PATENT DOCUMENTS

| | | |
|---|---|---|
| 6,458,776 B1 | 10/2002 | Ekwuribe et al. |
| 6,475,518 B1 | 11/2002 | Baumgart et al. |
| 6,517,871 B1 | 2/2003 | Venkatesh et al. |
| 6,551,620 B2 | 4/2003 | Otterbeck |
| 6,551,632 B2 | 4/2003 | Borody |
| 6,562,629 B1 | 5/2003 | Lin et al. |
| 6,562,871 B1 | 5/2003 | Cappola |
| 6,583,128 B2 | 6/2003 | Ekwuribe et al. |
| 6,683,102 B2 | 1/2004 | Scaife et al. |
| 6,861,053 B1 | 3/2005 | Lin et al. |
| 7,452,872 B2 | 11/2008 | Johnson |
| 7,625,884 B2 | 12/2009 | Johnson |
| 2002/0049186 A1 | 4/2002 | Ekwuribe et al. |
| 2003/0078205 A1 | 4/2003 | Podolsky |
| 2003/0133983 A1 | 7/2003 | Otterbeck |
| 2003/0138399 A1 | 7/2003 | Anton et al. |
| 2003/0190352 A1 | 10/2003 | Escoi et al. |
| 2005/0090473 A1 | 4/2005 | Devane et al. |
| 2005/0169996 A1 | 8/2005 | Dittmar et al. |
| 2006/0223787 A1 | 10/2006 | Devane et al. |
| 2008/0096849 A1 | 4/2008 | Johnson |
| 2009/0252788 A1 | 10/2009 | Lockhart et al. |
| 2010/0048519 A1 | 2/2010 | Yeh et al. |
| 2016/0279153 A1 | 9/2016 | Lockhart et al. |

FOREIGN PATENT DOCUMENTS

| | | |
|---|---|---|
| JP | 08-169847 A | 7/1996 |
| WO | 1992/06679 A1 | 4/1992 |
| WO | 1992/06690 A1 | 4/1992 |
| WO | 1992/016206 A1 | 10/1992 |
| WO | 1992/016214 A1 | 10/1992 |
| WO | 1995/18622 A1 | 7/1995 |
| WO | 1998/41212 | 9/1998 |
| WO | 1999/57134 A1 | 11/1999 |
| WO | 2000/045803 A2 | 8/2000 |
| WO | 2004/012699 A2 | 2/2004 |
| WO | 2004/082715 A1 | 9/2004 |
| WO | 2005/021009 | 3/2005 |
| WO | 2005/030173 A1 | 4/2005 |
| WO | 2005/074908 A1 | 8/2005 |
| WO | 2007/025146 A2 | 3/2007 |
| WO | 2008/063211 A2 | 5/2008 |

OTHER PUBLICATIONS

Brennan et al., Effect of food on the pharmacokinetics (PK) of 5-ASA(M) and N-acetyl-5-asa (NM) after a single 1 GM eudragit-L 100-coated tablet dose of 5-ASA. Pharmaceutical Research (New York). 1994;11(Suppl. 10):S443.
Citizens Petition to the FDA, Amendment- Dissolution Supplement, Jun. 14, 2007.
Citizens Petition, Salix Pharmaceuticals, Inc.; Apr. 13, 2005, pp. 1-23.
Clinical Pharmacology and Biopharmaceutics Review Jun. 22, 2000, pp. 1-131.
Clinical Pharmacology and Biopharmaceutics Review, Reviewer Carol Cronenberg, NDA: 20-610, Submission Date Jun. 23, 1997, Document stamp date: May 19, 1998.
Colazal Label, 2000.
Colazal Label, 2008.
Colazal Package Insert, Dec. 2006.
Cosnes et al., Gender differences in the response of colitis to smoking. Clin Gastroenterol Hepatol. Jan. 2004;2(1):41-8.
De Mey et al., Prandial and diurnal effects on the absorption of orally administered enteric coated 5-aminosalicylic acid (5-ASA). Br J Clin Pharmacol. Feb. 1992;33(2):179-82.
De Vos, Clinical pharmacokinetics of slow release mesalazine. Clin Pharmacokinet. Aug. 2000;39(2):85-97.
FDA Clinical Pharmacology and Biopharmaceutics Review(s) for NDA No. 20-6190 on Colazal Capsules, Jun. 22, 2000.
Food and Drug Administration, Letter. 1 page. Apr. 14, 2005.
Forbes et al., Pharmacokinetics of Balsalazide Sprinkled on Food or as Intact Capsules Administered Under Fasting of Fed Conditions in Healthy Volunteers. 3 pages. Dec. 1, 2006.
Godde, Bioavailability in mesalazine therapy: Microcapsules to optimize concentrations in the bowel. Krankenhauspharmazie. 1996;17(3):12 pages.
Goebell et al., Oroileal transit of slow release 5-aminosalicylic acid. Gut. May 1993;34(5):669-75.
Green et al., Balsalazide is more effective and better tolerated than mesalamine in the treatment of acute ulcerative colitis. The Abacus Investigator Group. Gastroenterology. Jan. 1998;114(1):15-22.
Hadziselimovic et al., Long-term 5-ASA treatment and gender-related differences in children with IBD. Autoimmune Diseases in Pediatric Gastroenterology, Proceedings of Falk Symposium 127, IV International Falk Symposium on Paediatric Gastroenterology. 2002. pp. 159-163. Abstract No. 24.
Hanauer, Update on mesalazine for inflammatory bowel disease. Research and Clinical Forums. 1998;20(1):203-208.
Hancock et al., The Relative Densities of Pharmaceutical Powders, Blends, Dry Granulations, and Immediate-Release Tablets. Pharm Tech. Apr. 2003. pp. 64-80. www.pharmtech.com.
Hussar, New drugs of 2001. J Am Pharm Assoc (Wash). Mar.-Apr. 2002;42(2):227-63.
Jahraus et al., Prevention of acute radiation enteritis in patients receiving radiotherapy for prostate cancer: early results of a randomized double-blind placebo-controlled trial of balsalazide. American Journal of Gastroenterology. Oct. 2004;99(10):5284-5285, Abstract No. 871.
Jahraus et al., Randomized double-blind placebo-controlled trial of balsalazide in the prevention of acute radiation enteritis as a consequence of pelvic radiotherapy. I J Radiation Oncology. Proceedings of the 46th Annual ASTRO Meeting. Sep. 2004;v 60(1):S253-S254. Abstract No. 202.
Johnson, Balsalazide Fed v. Fasted Study. pp. 1-20. Feb. 3, 2007.
Johnson, Open Capsule Letter. Salix Pharmaceuticals, Inc. 2 pages. Feb. 2, 2001.
Järnerot, New salicylates as maintenance treatment in ulcerative colitis. Gut. Sep. 1994;35(9):1155-8.
Kamm et al., Drug management of ulcerative colitis. BMJ. Jul. 4, 1992;305(6844):35-8.
Keller et al., Significance of galenic preparations for luminal release of 5-aminosalicylic acid in human small Intestinal lumen. Medizinische Klinik (Munich, Germany: 1983), (May 15, 1998) vol. 93(5)294-299. Language: German (English Abstract).
Khan et al., Effect of variation in compaction force on properties of six direct compression tablet formulations. J Pharm Sci. Dec. 1976;65(12):1835-7.
Kilic et al., Double-blinded, randomized, placebo-controlled study to evaluate the effectiveness of sulphasalazine in preventing acute gastrointestinal complications due to radiotherapy. Radiother Oncol. Nov. 2000;57(2):125-9.
Klotz, Clinical pharmacokinetics of sulphasalazine, its metabolites and other prodrugs of 5-aminosalicylic acid. Clin Pharmacokinet. Jul.-Aug. 1985;10(4):285-302.
Korvick, NDA 20-610/S014 Letter to Ms. Kompa, Director of Regulartory Affairs. Department of Health and Human Services. 3 pages. Sep. 21, 2006.
Kruis et al., Low dose balsalazide (1.5 g twice daily) and mesalazine (0.5 g three times daily) maintained remission of ulcerative colitis but high dose balsalazide (3.0 g twice daily) was superior in preventing relapses. Gut. Dec. 2001;49(6):783-9.
Layer et al., Delivery and fate of oral mesalamine microgranules within the human small intestine. Gastroenterology. May 1995;108(5):1427-33.
Lialda™ (mesalamine) Delayed Release Tablets. Package Insert, Shire US Inc., 10 pages. 2007.
Mansfield et al., A double-blind comparison of balsalazide, 6.75 g, and sulfasalazine, 3 g, as sole therapy in the management of ulcerative colitis. Aliment Pharmacol Ther. Jan. 2002;16(1):69-77.
Martenson et al., Olsalazine is contraindicated during pelvic radiation therapy: results of a double-blind, randomized clinical trial. Int J Radiat Oncol Biol Phys. May 1, 1996;35(2):299-303.

(56) References Cited

OTHER PUBLICATIONS

McLachlan et al., Meals and medicines. Aust Prescriber. 2006;29(2):40-41.

McNeil, Pentasa Summary Basis for Approval, 79 pages. May 22, 1998.

Mols et al., Sulfasalazine transport in in-vitro, ex-vivo and in-vivo absorption models: contribution of efflux carriers and their modulation by co-administration of synthetic nature-identical fruit extracts. J Pharm Pharmacol. Dec. 2005;57(12):1565-73.

NDA 20-610 OmniChem Balsalazide DMF 1287 (1996), Sec 7, p. 22.

Norlander et al., Pharmacokinetics of a 5-aminosalicylic acid enteric-coated tablet and suppository dosage form. Aliment Pharmacol Ther. Aug. 1989;3(4):333-42.

Porter, Coating of Pharmaceutical Dosage Forms. Remington's Pharmaceutical Sciences, 18th Edition. Alfonso R. Gennaro (Ed.), Mack Publishing Company, Easton, Pennsylvania. Chapter 90, pp. 1666-1675 (1990).

Qureshi et al., Mesalamine delivery systems: do they really make much difference? Adv Drug Deliv Rev. Jan. 6, 2005;57(2):281-302.

Ragunath et al., Review article: balsalazide therapy in ulcerative colitis. Aliment Pharmacol Ther. Oct. 2001;15(10)1549-54.

Re: Docket No. 2005P-0146/CP1, SUP 1, SUP 2, SUP 3 & SUP 4; Food and Drug Administration, Dec. 28, 2007; pp. 1-27.

Reilly et al., Frontiers in Gastroenterology. Journal of Pharmacy Practice. 2002;15(3):241-249.

Resbeut et al., A randomized double blind placebo controlled multicenter study of mesalazine for the prevention of acute radiation enteritis. Radiother Oncol. Jul. 1997;44(1):59-63.

Rudnic et al., Oral Solid Dosage Forms. Remington's Pharmaceutical Sciences, 18th Edition. Alfonso R. Gennaro (Ed.), Mack Publishing Company, Easton, Pennsylvania. Chapter 89, pp. 1633-1665 (1990).

Ryde et al., The Pharmacokinetics of Olsalazine Sodium in Health Volunteers After a Single i.v. Dose and After Oral Doses with and without Food. Eur J Clin Pharmacol. 1988;34:481-488.

Salix Pharmaceuticals, Inc., NDA 20-610/S-014, Colazal® (balsalazide disodium) Capsules. pp. 3-11, Feb. 2006.

Salix Study No. MPPK 1002. "Granulated Mesalamine Food Effect Pk." Sep. 21, 2007, pp. 1-6.

Salix, Colazal "Food Effect" Application granted FDA approval. Biotech Business. Nov. 1, 2006;19(11):2 pages.

Sandborn et al., Systematic review: the pharmacokinetic profiles of oral mesalazine formulations and mesalazine pro-drugs used in the management of ulcerative colitis. Aliment Pharmacol Ther. Jan. 2003;17(1):29-42.

Schellekens et al., A novel dissolution method relevant to intestinal release behaviour and its application in the evaluation of modified release mesalazine products. Eur J Pharm Sci. Jan. 2007;30(1):15-20.

Schroeder et al., Coated oral 5-aminosalicylic acid therapy for mildly to moderately active ulcerative colitis. A randomized study. N Engl J Med. Dec. 24, 1987;317(26):1625-9.

Sleisenger & Fordtrans's Gastrointestinal and Liver Disease, 6th edition, pp. 593-596 (1998).

Supplement to Citizen Petition, Salix Pharmaceuticals, Inc.; Jul. 14, 2006; pp. 1-10.

Supplement to Citizen Petition, Salix Pharmaceuticals, Inc.; Jun. 14, 2007; pp. 1-15.

Supplement to Citizen Petition, Salix Pharmaceuticals, Inc.; Nov. 14, 2006; pp. 1-13.

Supplement to Citizen Petition, Salix Pharmaceuticals, Inc.; Sep. 27, 2007; pp. 1-7.

Truelove et al., Cortisone in ulcerative colitis; final report on a therapeutic trial. Br Med J. Oct. 29, 1955;2(4947):1041-8.

Tursi et al., Long-term treatment with mesalazine and rifaximin versus rifaximin alone for patients with recurrent attacks of acute diverticulitis of colon. Dig Liver Dis. Jul. 2002;34(7):510-5.

U.S. Department of Health and Human Services. Guidance for Industry: Food-Effect Bioavailability and Fed Bioequivalence Studies. Food and Drug Administration Center for Drug Evaluation and Research (CDER). Dec. 2002. 12 pages.

Wadworth et al., Olsalazine. A review of its pharmacodynamic and pharmacokinetic properties, and therapeutic potential in inflammatory bowel disease. Drugs. Apr. 1991;41(4):647-64.

Wilding et al., Gastrointestinal spread of oral prolonged-release mesalazine microgranules (Pentasa) dosed as either tablets or sachet. Aliment Pharmacol Ther. Feb. 2000;14(2):163-9.

Yakurigaku (Pharmacology), Nankodo Publishing, Aug. 1, 1997, Version 3, p. 582.

Yu et al., Effect of food coadministration on 5-aminosalicylic acid oral suspension bioavailability. Clin Pharmacol Ther. Jul. 1990;48(1):26-33.

USE OF AMINOSALICYLATES IN DIARRHOEA-PREDOMINENT IRRITABLE BOWEL SYNDROME

RELATED APPLICATIONS

This application is a continuation of U.S. application Ser. No. 14/585,911, filed Dec. 30, 2014; which is a continuation of U.S. application Ser. No. 13/742,837, filed on Jan. 16, 2013; which is a continuation of U.S. application Ser. No. 10/588,558, filed on May 25, 2007; which is a National Stage Application of Application No. PCT/AU2005/000142, filed on Feb. 4, 2005; which claims the benefit to the Australian Application No. 2004900563, filed Feb. 6, 2004. The entire contents of each of the aforementioned applications are hereby incorporated by reference.

TECHNICAL FIELD

This invention relates to the use of balsalazide for treatment of Non-Inflammatory Bowel Disease for example diverticulosis/diverticulitis, diarrhoea-predominant Irritable Bowel Syndrome (IBS), or other non-specific bowel disorders such as Irritable Bowel Syndrome (IBS) at times alternating with constipation.

BACKGROUND OF THE INVENTION

Diarrhoea-predominant IBS is a condition known to arise from non-obvious causes. In particular, Irritable Bowel Syndrome which is defined as being a non-inflammatory bowel disease is known not to be caused by any detectable infection by a pathogenic organism or organisms.

Irritable Bowel Syndrome is therefore not a form of Inflammatory Bowel Disease. Inflammatory Bowel Diseases are characterised by inflammation on histology and inflammation on colonoscopy whereas Irritable Bowel Syndrome shows no evidence of inflammation on colonoscopy and the histology shows no increase in inflammatory cells. Irritable Bowel Syndrome is therefore referred to as a "non specific" bowel disorder because there is no specific diagnostic criterion such as histology or a blood test that can diagnose it. Irritable Bowel Syndrome is only diagnosed when one excludes the presence of other "specific" diseases or disorders such as *Salmonella*, Gastroenteritis, *Campylobacter gastroenteritis*, *Clostridium difficile* infection, Giardiasis, Crohn's disease or Ulcerative colitis. Irritable Bowel Syndrome can be distinguished from infective and inflammatory bowel diseases such as colitis or Crohn's disease on culture or histological grounds and endoscopic appearances.

Irritable Bowel Syndrome is therefore a collection of symptoms such as bloating, diarrhoea, cramping, flatulence, or constipation where there is no specific diagnostic test that turns it into a specific bowel disorder. Irritable Bowel Syndrome may therefore be diagnosed by exclusion of other specific bowel disorders. Another example of a non specific gastrointestinal disorder is non ulcer dyspepsia.

The large bowel in man and to a lesser extent the small bowel, contain large concentrations of various enteric bacteria. Generally, patients will have no pain, cramping, diarrhoea or constipation if the bacterial contents are not infected with pathogenic strains which may colonise the bowel and remain there for prolonged periods of time. Acute infections and some chronic infections of the bowel flora however can cause inflammatory changes in the lining. When inflammation is visible this condition is called Inflammatory Bowel Disease (IBD), which can be transient or long term—for example 'ulcerative colitis'. In some forms of IBD the visible inflammation is absent and can only be detected by taking a biopsy and finding histological changes of inflammation. In this case the pathologist terms the IBD as "microscopic colitis".

Where there are no visible colonoscopic or histological abnormalities in the colon and when the stool tests are negative for any known infection, and yet the patient complains of symptoms referrable to the colon, such as urgency, diarrhoea, flatulence, cramping—the diagnosis of Irritable Bowel Syndrome can be made. Between 5% and 25% of the western population in different age groups may suffer from this disorder which has also been termed spastic colon, unstable colonic neurosis, spastic colitis or mucous colitis. In a classic case there is a triad of symptoms including low abdominal pain relieved by defecation, alternating constipation/diarrhoea and the passage of small calibre stools. In some patients there may be accompanying watery diarrhoea with or without pain. Distension, flatulence, wind and at times nausea and headaches may also be accompanying systemic symptoms. At times diarrhoea alternates with constipation.

The pathogenesis of IBS is unclear. Emotional disturbances, fibre deficiency, purgative abuse and food intolerance have been some of the implicated aetiological agents but none have been proven nor well demonstrated. Evidence is therefore lacking for an infective cause or auto-immunity. Conventional treatments for IBS have been unsatisfactory as exemplified by the large number of therapies that have from time to time been recommended or trialed. These have included psychotherapy, dietary regimens, anti-spasm agents, anti-cholinergics, anti-depressants, bulking agents, various receptor antagonists, carminatives, opiates, and tranquillisers—all without substantial success. Indeed there is no evidence that cure is possible. Yet IBS is one of the most common of all the gastrointestinal illnesses and though not life-threatening, causes great distress especially to those severely affected, and may bring a feeling of frustration and helplessness, being generally lifelong. In particular, diarrhoea-predominant IBS can cause incontinence in some patients and, for example, the inability of being sure that one can reach ones employment causing some to drive from rest room to rest room on their way to work. In some patients urgency is so severe that they can only hold their motions for a few seconds.

One treatment that has been proposed for the treatment of IBS and for other bowel diseases is the use of certain classes of aminosalicylic acids. For example Borody in U.S. Pat. No. 5,519,014 describes the use of 5-aminosalicylic acids (5-ASA compounds) for the treatment of IBS. Similarly, Lin et al (U.S. Pat. No. 6,326,364) teaches that 5-ASA compounds can inhibit clostridia (a pathogen).

Whilst prior art methods go some way to treating IBS, there is a need for other treatment regimes and in particular treatment regimes for non-specific bowel disorders such as diarrhoea-predominant IBS which may not be effectively treated by prior art methods.

OBJECT OF THE INVENTION

It is an object of the present invention, at least in preferred embodiments to overcome or substantially ameliorate at least one of the above disadvantages or at least provide a suitable alternative.

SUMMARY OF THE INVENTION

According to a first aspect, there is provided a method for the treatment or prophylaxis of non-inflammatory bowel diseases, diarrhoea-predominant irritable bowel syndrome or other non-specific bowel disorder comprising administering to a patient in need of such treatment or prophylaxis an effective amount of balsalazide or a salt or a derivative thereof or a composition comprising balsalazide or a salt or a derivative thereof together with a suitable carrier.

In one embodiment, in a sub-group of patients the method alleviates symptoms of alternating diarrhoea and constipation type Irritable Bowel Syndrome or constipation-predominant Irritable Bowel Syndrome.

According to a second aspect, there is provided a method for the treatment or prophylaxis of non-inflammatory bowel diseases, diarrhoea-predominant irritable bowel syndrome or other non-specific bowel disorder comprising administering to a patient in need of such treatment or prophylaxis an effective amount of a 4-ASA or 5-ASA compound modified to include a 4-ABA side chain, or a salt or a derivative thereof or a composition comprising the modified compound or a salt or a derivative thereof together with a suitable carrier.

According to a third aspect, there is provided use of balsalazide or a salt or derivative thereof for the manufacture of a medicament for the treatment or prophylaxis of non-inflammatory bowel diseases, diarrhoea-predominant Irritable Bowel Syndrome or other non-specific bowel disorder.

According to a fourth aspect, there is provided use of a 4-ASA or 5-ASA compound modified to include a 4-ABA side chain, or a salt or derivative thereof for the manufacture of a medicament for the treatment or prophylaxis of non-inflammatory bowel diseases, diarrhoea-predominant Irritable Bowel Syndrome or other non-specific bowel disorder.

According to a fifth aspect, there is provided balsalazide or a salt or a derivative thereof or a composition comprising balsalazide or a salt or a derivative thereof together with a suitable carrier when used for the treatment or prophylaxis of non-inflammatory bowel diseases, diarrhoea-predominant Irritable Bowel Syndrome or other non-specific bowel disorder.

According to a sixth aspect, there is provided a 4-ASA or 5-ASA compound modified to include a 4-ABA side chain, or a salt or a derivative thereof or a composition comprising balsalazide or a salt or a derivative thereof together with a suitable carrier when used for the treatment or prophylaxis of non-inflammatory bowel diseases, diarrhoea-predominant Irritable Bowel Syndrome or other non-specific bowel disorder.

Definitions

The following definitions are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

All the references cited in this application are specifically incorporated by reference are incorporated herein in their entirety. However, inclusion of a specific reference herein is not intended to indicate that the reference is generally known in Australia or elsewhere.

DETAILED DESCRIPTION OF PREFERRED EMBODIMENTS

There is provided a method for the treatment or prophylaxis of non-inflammatory bowel diseases including diverticulosis/diverticulitis, diarrhoea-predominant irritable bowel syndrome or other non-specific bowel disorder including constipation, bloating, diarrhoea-constipation IBS or constipation IBS. The method comprises administering to a patient in need of such treatment or prophylaxis an effective amount of balsalazide or a salt or a derivative thereof or a composition comprising balsalazide or a salt or a derivative thereof together with a suitable carrier. The patient may be a mammal including a human.

Balsalazide corresponds to the formula

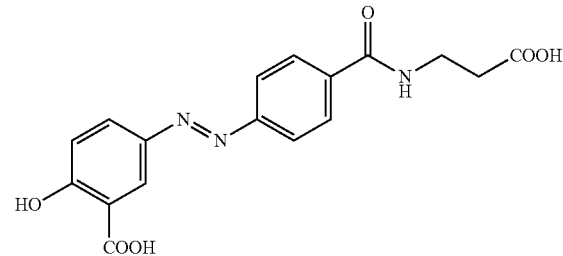 [SMILES: O=C(O)CCNC(=O)c1ccc(/N=N/c2ccc(O)c(C(=O)O)c2)cc1]

and is 5-[(1E)-[4-[[(2-carboxyethyl)amino]carbonyl]phenyl]azo]-2-hydroxybenzoic acid.

The present invention arose from the discovery by the inventors that treatment of patients with non infectious bowel disorders with 5ASA compounds such as mesalazine and olsalazine or with 4ASA compounds such as 4-aminosalicylic acid, whether alone or in combination with 5ASA compounds, whilst capable of suppressing symptoms in most patients with diarrhoea-predominant IBS symptoms may be even more effective when balsalazide is administered alone or in combination. From clinical experience, it has been found by the inventor that balsalazide is much more powerful at suppressing the symptoms of diarrhoea-predominant Irritable Bowel Syndrome than the conventional 4ASA and 5ASA compounds. Balsalazide is better than mesalazine (5-ASA) in controlling and may inhibit even more powerfully the symptoms of diarrhoea-predominant IBS and associated conditions enumerated below. This is unexpected. It was not expected that balsalazide would be capable of treating diarrhoea-predominant IBS as it is a very different molecule to the conventional 4ASA and 5ASA compounds. Balsalazide (5-[(1E)-[4-[[(2-carboxyethyl)amino]carbonyl]phenyl]azo-2-hydroxybenzoic acid and its sodium salt, molecular weight 437.32 (formula $C_{17}H_{13}N_3O_6Na_2 \cdot 2H_2O$), is composed of a 5-amino salicylic acid joined to an unusually long chain, 4-amino benzoyl-β-alanine (4-ABA). It is therefore a much larger molecule and does not belong to the same molecular shape as mesalazine or olsalazine. The inventors noted that balsalazide can substantially inhibit the symptoms of diarrhoea in patients with diarrhoea-predominant IBS. It is thought that this is due to a large extent to the properties of the unique 'inactive carrier' side chain (4-ABA). It is noted that the side chain together with the 5-ASA potentiates inhibition of gas production, cramping, fluid secretion, and mucus production. It appears the large side chain apart from the salicylate component is effective in treating diarrhoea. In addition, in a subgroup of patients the constipation component of IBS may respond to the same treatment.

Although it is reported that balsalazide is an analogue of 5-aminosalicylic acid, while not wishing to be bound to any theory, in the present method it would appear that it is not the 5-ASA group that is functioning in diarrhoea control but the large side chain 4-ABA appears to be the active component. Other 5-ASA or 4-ASA compounds modified to include the 4-ABA side chain may also be effective in the inventive methods. The compounds may also be used to treat other non-specific disorders such as non-ulcer dyspepsia.

Hence, the invention provides a method of treatment or prophylaxis of non-inflammatory bowel diseases, diarrhoea-predominant Irritable Bowel Syndrome and other non-specific bowel disorders and their associated symptoms comprising a step of dosing a patient suffering therefrom with balsalazide or a derivative or salt thereof. Other non-specific bowel disorders includes any disorder diagnosed by exclusion of other specific bowel disorders such as non-ulcer dyspepsia, alternating diarrhoea and constipation type Irritable Bowel Syndrome, Constipation-predominant Irritable Bowel Syndrome, constipation or bloating. Non-inflammatory bowel diseases includes diverticulosis or diverticulitis.

In one embodiment, the invention provides a method for the treatment or prophylaxis of one or more of Non-inflammatory Bowel Disease, diverticulosis, diverticulitis, diarrhoea-predominant Irritable Bowel Syndrome, Irritable Bowel Syndrome, bloating, diarrhoea, cramping, pain, low abdominal pain, distension, wind, flatulence, gas production, fluid secretion, mucus production, constipation, urgency, non ulcer dyspepsia, spastic colon, unstable colonic neurosis, spastic colitis, mucous colitis, alternating constipation/diarrhoea, incontinence, alternating diarrhoea and constipation type IBS or constipation IBS.

There is also provided balsalazide or a derivative or salt thereof used for treatment or prophylaxis of non-specific bowel disorders, particularly diarrhoea-predominant LBS.

There is also provided use of balsalazide or a derivative or salt thereof in the manufacture of medicament with said balsalazide, derivative or salt thereof as the base product with or without accompanying supportive or combination active and inactive agents. The supportive or combination active and inactive agents may be administered together with balsalazide. Such administration may or may not be coincidental administration. For example, the active agents may be administered as a single combined composition or may be administered as separate entities in such a manner as to have overlapping therapeutic profiles. When administered as separate entities, the active agents may be administered in any order as determined by the treating physician.

The supportive or combination agents may contain, amongst others, separate 5-ASA or 4-ASA compounds, such as mesalazine (5-amino salicyclic acid), olsalazine, sulfasalazine, ipsalazide, benzalazine, para-amino salicylic acid (4-amino salicylic acid) and pharmaceutical acceptable salts thereof A combination of balsalazide and olsalazine, for example together in a single capsule or separately administered, may be used to treat both diarrhoea and constipation predominant IBS since olsalazine does secrete water into the bowel. Mesalazine together with balsalazide may also be combined for diarrhoea predominant IBS. Such a combination is synergistic with amplification of the combined individual activities. In this regard it appears that the side chain of balsalazide may have antimicrobial activity. When combined with mesalazine, which has specific activity against *Clostridium difficile* in patients with IBS/diarrhoea who have mixed infections, balsalazide and mesalazine provide a synergistic combination in the control of diarrhoea.

Other supportive or combination ingredients include anticholinergics, probiotics (eg., lactobacilli, bifodobacteria, clostridia such as *Clostridium butyricum,*bacteroides, *E coli* and others), acceptable antibiotics (eg., rifamycins such as rifabutin, rifampicin, refalazil, rifaximin and others; neomycin, vancomycin, tetracyclines), anti-spasm medications (e.g. dicyclomine), as well as various excipients.

The medicament/composition for use in the invention may be prepared by means known in the art for the preparation of pharmaceutical compositions including blending, grinding, homogenising, suspending, dissolving, emulsifying, dispersing and, where appropriate, mixing of the balsalazide and where present other amino-salicylic acid derivative(s), optionally together with one or more selected excipients, diluents, carriers and adjuvants and optionally together with one or more supportive combination ingredients.

The medicament/composition of the invention may be in the form of a tablet, lozenge, pill, troche, capsule, soft-gel capsule, sachet or other vehicle, elixir, powder, including lyophilised powder, solution, granule, suspension, emulsion, syrup or tincture including any form suitable for preparation as a rectal enema. Slow-release, or delayed-release forms may also be prepared, for example in the form of coated particles, multi-layer tablets or microgranules. The composition may also be presented in a compliance-enhancing blister pack.

Solid forms for oral administration may contain pharmaceutically acceptable binders, sweeteners, disintegrating agents, diluents, flavourings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, betonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. For administration as a tablet or capsule, the balsalazide may be combined in powdered or granulated form, for example by compression into a tablet or as a filling for a capsule. Alternatively, the balsalazide may be provided in the form of a tablet/capsule containing the balsalazide in a microencapsulated form.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further include dispersing agents and/or suspending agents. Suitable suspending agents include sodium carboxymethylcellulose, methylcellulose, hydroxypropylmethyl-cellulose, poly-vinyl-pyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further include one or more emulsifying agents. Suitable emulsifying agents include dispersing agents as exemplified above or natural gums such as gum acacia or gum tragacanth.

Typically the disodium salt of balsalazide will be used. However any other salt or derivative or prodrug can be used. Accordingly where reference herein is made to balsalazide, the salt, prodrug or derivative thereof is likewise referenced.

The active ingredient may be incorporated with the pharmaceutically acceptable excipient/s in any suitable form, including but not limited to tablets, lozenges, pills, troche, capsules, soft-gel capsules or as powder in sachets. It may also be presented as granulated medication in larger volumes in sachets. The capsules, tablets or sachets may be taken one or more times per day in balsalazide doses ranging from 100 mg to 30 grams per day, for example 100 mg, 200 mg, 300 mg, 400 mg, 500 mg, 600 mg, 700 mg, 800 mg, 900 mg, 1000 mg, 2 g, 3 g, 4 g, 5 g, 6 g, 7 g, 8 g, 9 g, 10 g, 11 g, 12 g, 13 g, 14 g, 15 g, 16 g, 17 g, 18 g, 19 g, 20 g, 21 g, 22 g, 23 g, 24 g, 25 g, 26 g, 27 g, 28 g, 29 g or 30 g per day or any selected amounts within this range. Agents may be enteric coated, and may take the form of slow-release format to reach both the upper and lower bowel. In one embodiment, the balsalazide is presented in a form which facilitates its release in the distal small bowel. For example, in a composition of the invention, the balsalazide may be provided with an enteric coating or provided in an enteric coated release capsule, or enteric coated microencapsulated particles can be carried within a capsule of a distally-releasing amino-salicylic acid, for example olsalazine. Suitable materials for enteric coating are known in the art and include various synthetic resins bearing carboxyl groups, phenyl salicylate, and shellac. Examples of such enteric coating materials are polyrnethacrylic acid and methacrylic acid copolymers such as methacrylic acid-acrylic acid ester copolymers; modified cellulose esters such as hydroxypropyl cellulose phthalate, hydroxypropyl methylcellulose phthalate, ethyl cellulose phthalate, methyl cellulose phthalate and mixtures thereof, cellulose acetate phthalate, hydroxypropyl methylcellulose succinate, ethyl cellulose succinate, methyl cellulose succinate and mixtures thereof, cellulose acetate trimellitate, cellulose ether phthalates; and polyvinyl acetate phthalate, succinate or trimellitate. In one embodiment the enteric coating is Opadry OY-P 22920, available from Colorcon, 415 Moyer Blvd, West Point, Pa. 19486, United States of America. Enteric film-forming compositions are described, for example, in U.S. Pat. Nos. 4,556,552 and 4,704,295, the disclosures of which are incorporated herein by reference.

Generally for long term therapy dosage may typically commence at a lower level, such as daily and build up to the desired full amount over several weeks, such as twice or three times daily if required. The invention also extends in one embodiment to multiple packages of individual dosages to be taken in sequence to provide such a gradual build up. The balsalazide may therefore be taken once, twice, three times a day or more frequently. In one embodiment, balsalazide is administered twice daily. Administration may be over a period of 1 to 60 days or more, including indefinitely for the lifetime of the patient. For example the balsalazide may be administered over 1, 2, 3, 4, 5, 6 days, 1 week, 2 weeks, 3 weeks, 4 weeks, 1 month, 2 months or more. After relief of symptoms is achieved, administration of balsalazide may be ceased, tapered, or continued for an indefinite period, for example including reduction to lower maintenance dosages.

Any suitable dosage and method of administration may be utilized, as determined by the treating physician. Typically this may be orally or as a rectal enema. In one embodiment, the medicament/composition may be administered orally at a dose generally of about 3 grams balsalazide per day, this dose being the ideal dose. In another embodiment for clinical use, a balsalazide dose of between about 1 gram and 4 grams may be used by patients either as a twice daily or three times daily dosage.

With the foregoing it will be appreciated that a new use has been discovered for balsalazide where previously no such effect has been described, and that actions of balsalazide can be further potentiated, even synergistically, by the addition of further agents.

EXAMPLES

The present invention will now be described by way of example. The examples should not be construed as in any way limiting the scope of the invention.

Example 1

A 34 year old female presented with a 7 year history of worsening diarrhoea (watery 6-12/day), urgency, cramping lower abdominal pain and at times faecal incontinence. There was no clear preceding illness nor antibiotic usage. She underwent numerous investigations, beginning with general practitioners ordering stool cultures, blood tests, ultrasound and CT scan examinations. With the passage of time she noticed that some foods caused worsening of symptoms, and was told by a naturopath that she suffered from a 'food allergy'. The patient restricted her diet and this gave her some benefit in reducing the symptoms but resulted in progressive weight loss. She consulted a gastroenterologist and underwent endoscopic small bowel biopsy—where coeliac disease was excluded histologically—and colonoscopy with biopsy and further stool cultures. All tests being non-diagnostic, she was told she had severe, diarrhoea-predominant IBS. She continued on the restricted diet, and was referred for counselling and hypnotherapy. Over the next 6-12 months she progressively lost weight with only modest control of her symptoms by the diet. Within 2 weeks of commencing increasing doses of balsalazide from 1.5 gram to 3 grams per day, the stools progressively formed up, with frequency reducing to 1-2 formed stools per day. Pain was completely abolished, urgency disappaeared and she broadened her diet. By 6 weeks of treatment she regained 7 kg in weight. She continues to be virtually completely symptom-free on balsalazide at 26 weeks.

Example 2

A 67 year old female complained of greater than 20 years of diarrhoea with intervening constipation, abdominal bloating, pains, flatulence, and nausea with acid reflux. She had undergone several complete medical investigations including stool tests, blood tests, X-ray imaging and colonoscopic examinations, with negative findings apart from the presence of diverticulosis. Diagnosed as chronic IBS she tried increasing fibre intake, controlling stress, and changing her diet, all to no avail. On commencing balsalazide 1.5 g/day and pushing the dose upwards to 4.5 g/d her diarrhoea, pains, flatulence and nausea abated. At the higher dose the constipation also disappeared. The improvements remain sustained at 26 weeks.

Example 3

A 28 year old male was referred because of long standing diarrhoea predominant Irritable Bowel Syndrome. This was described as being "porridgy" and sometimes watery or explosive and associated with cramping abdominal pain which passed through to his back. There was no bloating but there was marked flatulence, no nausea and some acid reflux. The man had previously been extensively investigated with tests such as stool tests and colonoscopic examinations finding no cause for his symptoms. Having tried a number of standard therapies the man presented for further investigations. Because ongoing trials with patients with diarrhoea-predominant IBS was being carried out, the male patient commenced with a trial product (Salofalk™ oral granules, 1 gram, twice daily). Salofalk™ is a particular form of 5 Aminosalicylic acid (mesalazine) which has been found to be useful in patients with the condition. The symptoms however continued. Even after progressively raising the dose to 2 grams twice daily, and then to 3 grams twice daily, the symptoms still continued, albeit slightly reduced in severity. The male patient was not prepared to go to a higher dose (such a dose is also not used clinically).

The male patient was offered treatment with balsalazide in accordance with the present invention. The balsalazide was not immediately available and after several weeks, the patients symptoms returned to a severe level. Balsalazide was commenced at a dose of 750 mg twice daily and slowly raised to 1.5 grams twice daily. Improvement in symptoms was dramatic and far outweighed the slight improvement with the higher doses of Salofalk™ granules. To attempt to completely control the mans symptoms, the patient was treated with a dose of 3 grams balsalazide twice daily (gram equivalent to Salofalk™). The patients symptoms largely disappeared. The patient had two formed stools per day without any urgency or flatulence and was able to eat foods he previously would not have considered ingesting. The improvements were sustained at four months follow up.

This example shows clinically the difference between the use of standard mesalazine and the use of balsalazide in accordance the invention in diarrhoea-predominant IBS.

INDUSTRIAL APPLICABILITY

The present invention relates to a method of treating or preventing non-inflammatory bowel diseases, diarrhoea-predominant irritable bowel syndrome or other non-specific bowel disorders.

Other embodiments of the invention will be apparent to those skilled in the art from consideration of the specification and practice of the invention disclosed herein.

The claims defining the invention are as follows:

1. A method for the treatment or prophylaxis of alternating diarrhoea and constipation type irritable bowel syndrome comprising administering to a patient in need of such treatment or prophylaxis between about 1 gram and about 4 grams of balsalazide or a salt thereof and rifaximin.

2. The method according to claim 1, wherein the patient is a mammal.

3. The method according to claim 2, wherein the patient is a human.

4. The method of claim 1, wherein the disodium salt of balsalazide is administered.

5. The method of claim 1, wherein about 3 grams of balsalazide is administered.

6. The method of claim 1, wherein the balsalazide is administered orally.

7. A method for the treatment or prophylaxis of constipation-predominant type irritable bowel syndrome comprising administering to a patient in need of such treatment or prophylaxis between about 1 gram and about 4 grams of balsalazide or a salt thereof and rifaximin.

8. The method according to claim 7, wherein the patient is a mammal.

9. The method according to claim 8, wherein the patient is a human.

10. The method of claim 7, wherein the disodium salt of balsalazide is administered.

11. The method of claim 7, wherein about 3 grams of balsalazide is administered.

12. The method of claim 7, wherein the balsalazide is administered orally.

* * * * *